US008912234B2

(12) United States Patent
Souto et al.

(10) Patent No.: US 8,912,234 B2
(45) Date of Patent: Dec. 16, 2014

(54) COMPOSITION CONTAINING RESVERATROL AND/OR DERIVATIVES THEREOF AND PLANT OIL, PROCESS FOR PRODUCING SAID COMPOSITION, NUTRACEUTICAL AND/OR PHARMACEUTICAL PRODUCT, AND METHOD FOR ENHANCING THE POTENTIAL OF RESVERATROL

(75) Inventors: Andre Arigony Souto, Porto Alegre (BR); Maria Martha Campos, Porto Alegre (BR); Fernanda Bueno Morrone, Porto Alegre (BR); Rodrigo Braccini Madeira da Silva, Porto Alegre (BR); Izaque de Sousa Maciel, Porto Alegre (BR)

(73) Assignee: UNIAO Brasileria de Educacao e Assistencia—Mantenedora da PUCRS, Porto Alegre (BR)

( * ) Notice: Subject to any disclaimer, the term of this patent is extended or adjusted under 35 U.S.C. 154(b) by 489 days.

(21) Appl. No.: 13/578,597

(22) PCT Filed: Feb. 10, 2010

(86) PCT No.: PCT/BR2010/000024
§ 371 (c)(1),
(2), (4) Date: Oct. 14, 2012

(87) PCT Pub. No.: WO2010/091488
PCT Pub. Date: Aug. 19, 2010

(65) Prior Publication Data
US 2013/0040920 A1   Feb. 14, 2013

(30) Foreign Application Priority Data
Feb. 10, 2009   (BR) ................................ 0900400

(51) Int. Cl.
| A61K 31/045 | (2006.01) |
| A61K 31/715 | (2006.01) |
| A61K 36/88  | (2006.01) |
| A23D 9/007  | (2006.01) |
| A23D 9/06   | (2006.01) |
| A23L 1/30   | (2006.01) |
| A61K 8/34   | (2006.01) |
| A61K 8/92   | (2006.01) |
| A61K 31/05  | (2006.01) |
| A61Q 19/00  | (2006.01) |
| A61K 31/724 | (2006.01) |

(52) U.S. Cl.
CPC .............. *A61K 36/88* (2013.01); *A61K 31/724* (2013.01); *A23D 9/007* (2013.01); *A23D 9/06* (2013.01); *A23L 1/3002* (2013.01); *A61K 8/347* (2013.01); *A61K 8/922* (2013.01); *A61K 31/05* (2013.01); *A61Q 19/00* (2013.01)
USPC ............................................. 514/728; 514/58

(58) Field of Classification Search
CPC .............................. A61K 31/05; A61K 31/724
USPC ...................................................... 514/728, 58
See application file for complete search history.

(56) References Cited

FOREIGN PATENT DOCUMENTS

JP   2006347928 A  * 12/2006
WO  WO 2009003798 A1 *  1/2009

OTHER PUBLICATIONS

JP 2006347928 A,(Dec. 2006), English translation abstract.*

* cited by examiner

*Primary Examiner* — Kevin E Weddington
(74) *Attorney, Agent, or Firm* — Laurence P. Colton; Smith Risley Tempel Santos LLC

(57) ABSTRACT

The present invention is a method for obtaining a formulation of resveratrol and rice bran oil. The resulting product in the form of an oil or solid proves to increase the therapeutic potential of resveratrol by the synergistic action of the components of the rice oil.

The product obtained through the method of the invention is an active principle which, when incorporated in nutraceutical and/or pharmaceutical compositions, provides antioxidant, anti-inflammatory, antiviral, cardioprotective, neuroprotective and/or cancer chemoprotective action, besides protecting against infections and ischemia, reducing obesity, and preventing illnesses of old age.

33 Claims, 5 Drawing Sheets

COMPOSITION CONTAINING RESVERATROL AND/OR DERIVATIVES THEREOF AND PLANT OIL, PROCESS FOR PRODUCING SAID COMPOSITION, NUTRACEUTICAL AND/OR PHARMACEUTICAL PRODUCT, AND METHOD FOR ENHANCING THE POTENTIAL OF RESVERATROL

FIELD OF THE INVENTION

The present invention is a method for obtaining a formulation of resveratrol and rice bran oil. The resulting product in the form of an oil or solid proves to increase the therapeutic potential of resveratrol by the synergistic action of the components of the rice oil.

The product obtained through the method of the invention is an active principle which, when incorporated in nutraceutical and/or pharmaceutical compositions, provides antioxidant, anti-inflammatory, antiviral, cardioprotective, neuroprotective and/or cancer chemoprotective action, besides protecting against infections and ischemia, reducing obesity, and preventing illnesses of old age.

ANTECEDENTS OF THE INVENTION

Trans-resveratrol (3,5,4'-trihydroxystilbene) has antioxidant, anti-inflammatory, antiviral, cardioprotective, neuroprotective cancer chemoprotective action, besides protecting against infections and ischemia, reducing obesity, and preventing aging. Trans-resveratrol is a polyphenol that can be found primarily in the skin of dark grapes and red wine. The more deep the color of the wine or the grapes, the greater the content of polyphenols. Studies seem to indicate that trans-resveratrol can help diminish the levels of low-density lipoproteins, also known as LDL cholesterol or "bad" cholesterol, and increase the levels of high-density lipoproteins, HDL cholesterol or "good" cholesterol. LDL primarily in its oxidized state can build up on the walls of the blood vessels, resulting in formation of atheroma plaques. These plaques are at the origin of atherosclerosis, which results in the obstruction of the blood vessels. Trans-resveratrol promotes the production of HDL by the liver, reduction of the production of LDL, and prevents the oxidation of the circulating LDL, thus having a role in reducing the risk of developing cardiovascular diseases, such as myocardial infarction.

Trans-resveratrol is also well known as a modulator of the expression and the activity of a class of protein known as sirtuin. By a modulator of sirtuins is meant compounds which regulate to increase (by activating or stimulating), to decrease (by inhibiting or suppressing), or otherwise change the functional property or the biological activity of the sirtuin protein.

Sirtuin is a member of the family of deacetylase proteins, the sirtuins, or preferably the family Sir2, which includes the Sir2 of yeast (GenBank Accession No P53685), C. elegans Sir-2.1 (GenBank Accession No NP_501912), and human SIRT1 (GenBank Accession No. NM_012238 and NP_036370 or AF083106) and SIRT2 (GenBank Accession No NM_012237, NM_030593, NP_036369, NP_085096, and AF083107).

Modulators of the sirtuin protein such as trans-resveratrol act to minimize or eliminate diseases connected with old age—chronic-degenerative diseases of the circulatory and neurological system, such as diseases of the eye (WO 2006/127987), mental pathologies (WO 2006/138418), diabetes (WO 2006/104586), cancer (WO 2006/102557), obesity (US 2006/111435).

Meanwhile, trans-resveratrol has low bioavailability; when administered orally, this molecule is quickly metabolized to form various derivatives that are quickly eliminated in the body, making its uptake difficult, and this is a technological problem waiting to be solved. One strategy for increasing the absorption of resveratrol is to mix it with chemical compounds that that compete for or inhibit these metabolic routes [of] derivatization. One commercial product that has this synergistic effect is Longevinex (www.longevinex.com), which is a formulation of trans-resveratrol, grape extract, and quercetin.

The present invention is the development of a method and a product of a mixture of trans-resveratrol with rice bran oil. This oil contains high levels of tocopherols, tocotrienols, and phytosteroids, and is especially rich in gamma-orizanol.

Gamma-orizanol has more effective antioxidant action than the healthy tocopherols, since it is more resistant to heat. Among its many actions are effects on growth, fighting of headache and neck pain, minimizing of the symptoms of menopause, fighting anemia, treatment of stress-related ulcers and an aid in the treatment of circulatory diseases. The properties of orizanol allow for its broad use, both as a medication, in cosmetic composition, such as a skin anti-aging agent, and even as a drug to reduce LDL type cholesterol.

In the recent literature we have various examples of the potentiation of trans-resveratrol in compounds with other molecules, such as together with gamma-tocotrienol it suppresses proliferation of breast cancer cells (Hsieh, T C, et al. Int J Oncol. 2008 October; 33(4):851-9), with roscovitin it inhibits progression of leukemia cells type HL-60 (Komina, O, et al. *Biochem Pharmacol.* 2008 Dec. 1; 76(11):1554-62), with the tocopherols they regenerate the activity of resveratrol (Fang, J G, et al J. Agric. Food Chem., 2008, 56 (23), 11458-11463) and with 4-hydroxynonenal it augments the detoxifying capacity (Zhang, H. et al Arch Biochem Biophys. 2009 Jan. 1; 481(1):110-5).

The patent literature contains several documents related to methods of trans-resveratrol and rice bran oil. Although none of the documents found anticipates or even suggests, if only indirectly, the inventive concept of the present invention, some documents used as reference are cited here.

The patent applications US 2003/6638545, US 2003/6642277, US 2003/0133945, US 2008/0070991, WO 2000/064282, WO 2004/000043 and WO 2009/003798 [mention] trans-resveratrol as part of formulations of a food or nutritional supplement in the solid, semisolid and liquid state that are obtained through a physical mixture with other substances.

Other patent applications refer to the obtaining of a microemulsion or emulsion of oil with trans-resveratrol. The document US 2003/6660286 describes an emulsion with biosurfactants and alpha-tocopherol. US 2005/0196347 reports a spray emulsion based on oil/water. Document US 2006/011051 describes a composition with polyunsaturated fatty acids and US 2008/0085357 involves the formation of a microemulsion through vacuum elimination of the solvent to achieve the critical micellar concentration.

SUMMARY OF THE INVENTION

In a first aspect, the present invention provides a composition able to avoid the rapid elimination of resveratrol and/or its derivatives, increase its absorption, and consequently increase the therapeutic potential of resveratrol and/or its derivatives.

Therefore, one object of the present invention is a composition comprising:

a) vegetable oil;
b) resveratrol and/or its derivatives; and
c) an adequate vehicle.

In one preferred embodiment, the vegetable oil is rice bran oil and the composition is in the form of a powder.

Another object of the present invention is a method for production of a composition comprising vegetable oil and resveratrol and/or its derivatives, comprising the steps of:
a) dissolving of the resveratrol and/or its derivatives in alcohol;
b) adding of the vegetable oil to the solution of step a) under agitation and ultrasound bath.

In one preferred embodiment, the method of production of a powder composition additionally comprises the steps of:
c) adding of the solution obtained in b) to a suspension of cyclodextrin in water, under agitation;
d) adding of an adsorbent to remove the water.

Another object of the present invention is a nutraceutical and/or pharmaceutical composition comprising the composition which comprises vegetable oil and resveratrol and/or its derivatives.

Another object of the present invention is a method for increasing the potential of resveratrol in an animal involving the administering of a composition comprising resveratrol and/or its derivatives associated with a vegetable oil.

These and other objects of the present invention will be appreciated from the following detailed description.

DETAILED DESCRIPTION OF THE INVENTION

Figure 1:
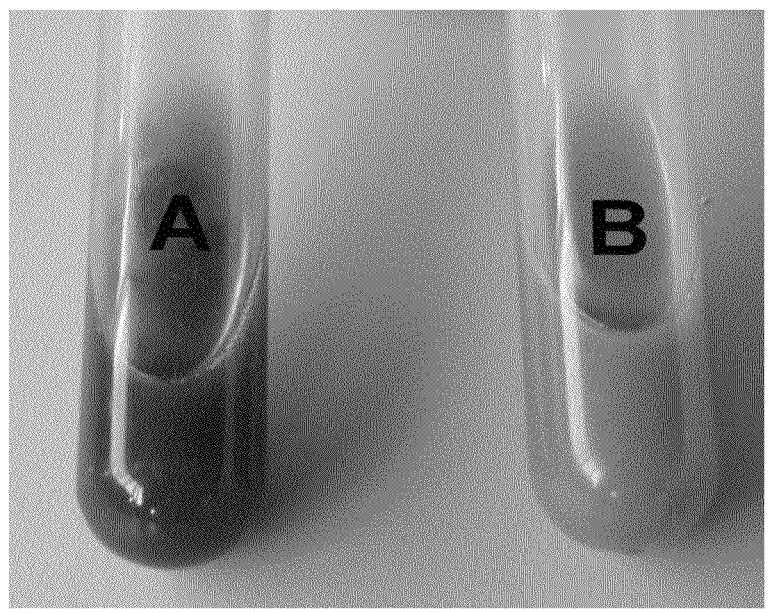
FIG. 1 shows two tubes, tube A is rice bran oil and tube B is rice oil plus trans-resveratrol.

The following examples illustrate, but do not limit the preferred ways of implementing the invention.

Composition

The present invention describes a composition able to avoid the rapid elimination of resveratrol and/or its derivatives, increase its absorption, and consequently increase the therapeutic potential of resveratrol and/or its derivatives. In particular, the composition comprises:
a) vegetable oil;
b) resveratrol and/or its derivatives; and
c) an adequate vehicle.

For purposes of the present invention, vegetable oil shall mean any oil, modified or not, derived from cereals chosen from the group comprising wheat, rice, rice bran, corn, millet, sorghum, rye, oats, barley, or combinations of these. Preferably, rice bran oil is used.

For purposes of the present invention, resveratrol and/or its derivatives shall mean the molecule of resveratrol, (3,5,4'-trihydroxy-trans-stilbene), also known as trans-resveratrol, and its methylated and/or acetylated derivatives.

The methylated derivatives can be: trans-3,5-dimethoxy-4'-hydroxyistilbene, trans-3,5,4"-trimethoxy-stilbene and trans-3,5-hydroxy-4'-methoxy-stilbene, described below.

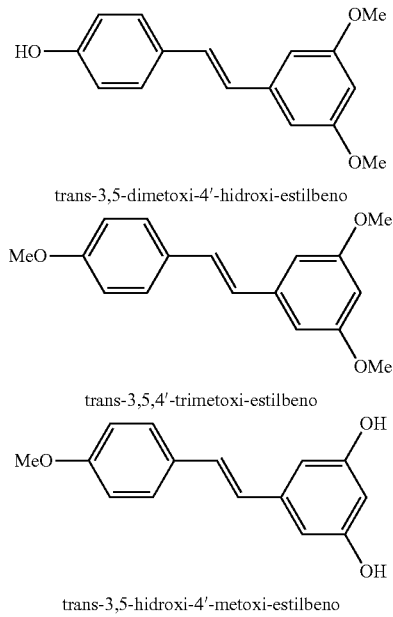

trans-3,5-dimetoxi-4'-hidroxi-estilbeno trans-3,5,4'-trimetoxi-estilbeno trans-3,5-hidroxi-4'-metoxi-estilbeno The acetylated derivatives can be: trans-3,5-diacetyl-4'-hydroxy-stilbene, trans-3,5,4'-triacetyl-stilbene and trans-3,5-hydroxy-4'-acetyl-stilbene, described below.

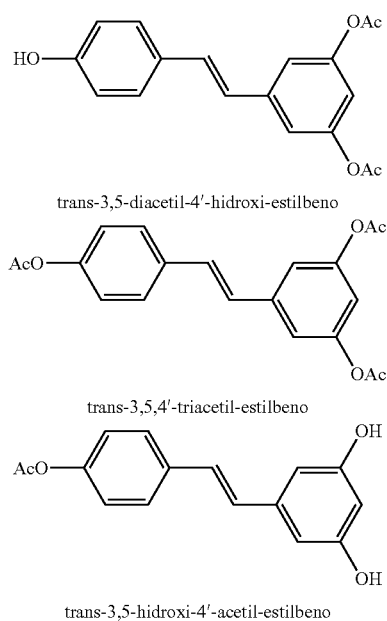

trans-3,5-diacetil-4'-hidroxi-estilbeno trans-3,5,4'-triacetil-estilbeno trans-3,5-hidroxi-4'-acetil-estilbeno Optionally, the composition can be in the form of a powder. In this embodiment, the composition also comprises cyclodextrin and an adsorbent. For purposes of the present invention, the cyclodextrins can be chosen from the group that comprises: α-cyclodextrin (α-CD), β-cyclodextrin (β-CD), γ-cyclodextrin (γ-CD), hydroxyethyl-β-CD, hydroxypropyl-β-CD, sulfobutylether-β-CD, methyl-β-CD, dimethyl-β-CD, random dimethylated-β-CD, random methylated-β-CD, carboxymethyl-β-CD, carboxymethyl ethyl-β-CD, diethyl-β-CD, tri-O-methyl-β-CD, tri-O-ethyl-β-CD, tri-O-butyryl-β-CD, tri-O-valeryl-β-CD, di-O-hexanoyl-β-CD, glucosyl-β-CD, maltosyl-β-CD and 2-hydroxy-3-trimethyl-ammoniopropyl-β-CD and combinations of these.

For purposes of the present invention, adequate adsorbents are any agents known in the prior art that are able to absorb water from the composition in order to maintain the powder form of the composition.

The adequate vehicle is any vehicle known in the prior art that is known for the intended use of the composition, which is that of a foodstuff.

In liquid compositions, the proportion of resveratrol and/or its derivatives to vegetable oil is comprised in the range of 1:80 to 1:90 (g of resveratrol and/or its derivatives to ml of vegetable oil). Preferably, the proportion is 1:83.33.

In powder compositions, the proportion of the oil/resveratrol mixture to cyclodextrin is comprised in the range of 1:0.2 to 1:0.25 (ml of oil/resveratrol mixture to g of cyclodextrin).

Both the liquid composition and the powder composition can be added to other nutritional components, thus yielding a nutraceutical product, or to medicinal components, thus yielding a pharmaceutical product. The quantity of the composition in this product varies from 0.001% wt/wt to 99% wt/wt of the product.

Method of Production of the Composition

The method for production of the composition of the present invention comprises the steps of:

a) dissolving of the resveratrol and/or its derivatives in alcohol;

b) adding of the vegetable oil to the solution of step a) under agitation and ultrasound bath.

In one preferred embodiment, the method of production of a powder composition additionally comprises the steps of:

c) adding of the solution obtained in b) to a suspension of cyclodextrin in water, under agitation;

d) adding of an adsorbent to remove the water.

The alcohol of step a) is preferably an alcohol containing 1 to 5 carbon atoms. In particular, ethanol will be used.

The trans-resveratrol used was obtained by the purification method as described in patent application PI0700152-5 or that acquired from the Sigma-Aldrich company. The beta-cyclodextrin (CAVAMAX W & Pharma) was acquired from the company ISP Technologies, Inc. The rice bran oil was obtained from the company A HELMUT TESSMANN ÓLEOS VEGETAIS (PI 0604880-3A) with the following composition: gamma-orizanol 1%; oleic acid 40%; linoleic acid 32%; linoleic acid[1] 1.5; vitamin E (tocopherol) 1,200 mg/kg

[1]Translation note: Possible mistake in the source file. The word, "linoléico," translated as "linoleic," appears twice. We believe one of these should be, "linolenic".

Method of Boosting the Potency of Resveratrol and/or its Derivatives

The method for boosting the potential of resveratrol in an animal comprising the administering of a composition comprising resveratrol and/or its derivatives associated with a vegetable oil.

By animal is meant any mammal, such as dogs, cats, horses and man.

Preferably, the animal is man.

The administering is done in a way known to the prior art, such as oral, topical, parenteral, enteral route.

Example 1

Obtaining of the Rice Bran Oil with 1.2% m/v of Trans-Resveratrol (Oil/Resv.)

Figure 2:
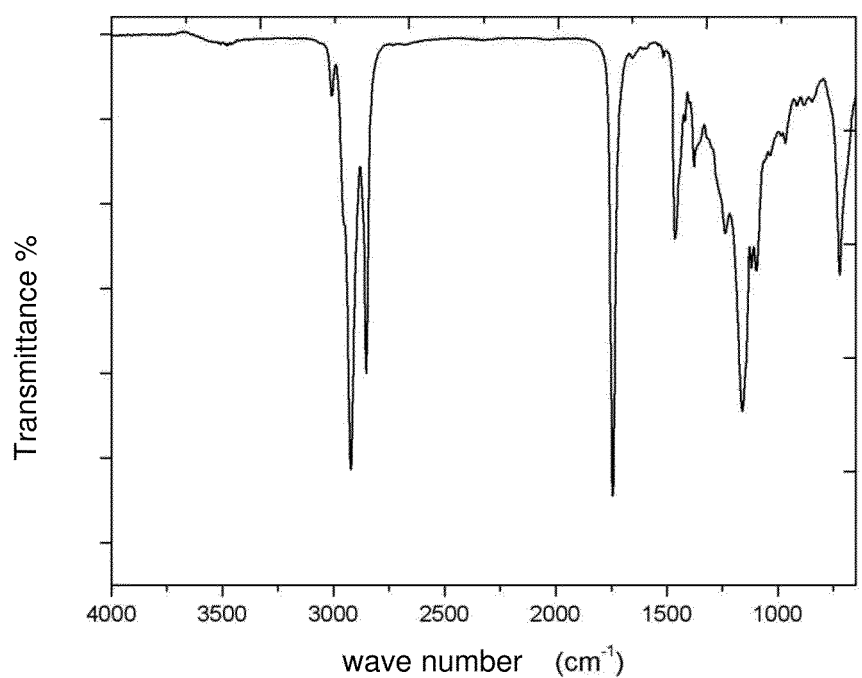
FIG. 2 shows the infrared spectrum of the product obtained from rice bran oil and trans-resveratrol.

In a 50 mL beaker there were placed 3 g of trans-resveratrol and up to 4 mL of 96% ethanol. The mixture was placed in the ultrasound bath for 30 min. After this, the mixture was added, a little at a time, to 250 mL of rice bran oil. The resulting mixture was agitated at 500 rpm for 30 min and then for 1 h in the ultrasound bath. The final product is viscous, brown in color (FIG. 1), and has a characteristic infrared spectrum (FIG. 2). The quantity of trans-resveratrol was [determined] by high-efficiency liquid chromatography (CLAE). For this quantification, an external calibration curve was constructed, with concentrations of trans-resveratrol varying between 0.10 and 200.0 mg·L-1. The CLAE was carried out with isocratic elution (flow rate of 1.0 mL min-1), using a 25% aqueous solution of acetonitrile, with pH 3.0, adjusted with H3PO4. The chromatograph was outfitted with a UV-VIS detector and a C18 column 250 mm in length, 5 μm particle diameter, and 4.6 mm internal diameter. The preparation of the sample is by the following steps: 10 g of the final product was mixed with 400 mL of methanol/acetone (7:3, v/v) and agitated (700 rpm) for 1 h at room temperature. The solution was cooled to −20 for 15 h. The liquid phase and the solid phase was separated by vacuum filtration. The solvent was removed [at] reduced pressure. The final product was diluted 1000 times in methanol and 20 μL were injected and detected at 306 nm. The concentration of resveratrol was 10.2±0.1 mg/1 mL.

Those skilled in the art will also recognize that the process of boosting the bioactivity of the invention can be applied to derivatives of resveratrol, such as its methylated and/or acetylated derivatives.

Example 2

Preparation of the Oil/Resv as a Powder

Figure 3:
FIG. 3 shows the oil/resveratrol in powder form.

In a 250 mL beaker containing 100 mL of oil/resv there were slowly added, with vigorous agitation (1000 rpm), 20 to 25 g of beta-cyclodextrin suspended in up to 10 mL of water over the course of 30 min. The mixture remained under agitation (800 rpm) for 1 hour. At the end, there was added up to 1% of celite. The final product has a powder form (FIG. 3). The quantity of trans-resveratrol was [determined] by high-efficiency liquid chromatography (CLAE). For this quantification, an external calibration curve was constructed, with concentrations of trans-resveratrol varying between 0.10 and 200.0 mg·L-1. The CLAE was carried out with isocratic elution (flow rate of 1.0 mL min-1), using a 25% aqueous solution of acetonitrile, with pH 3.0, adjusted with $H_3PO_4$. The chromatograph was outfitted with a UV-VIS detector and a C18 column 250 mm in length, 5 µm particle diameter, and 4.6 mm internal diameter. The preparation of the sample is by the following steps: 10 g of the final product was mixed with 400 mL of methanol/acetone (7:3, v/v) and agitated (700 rpm) for 1 h at room temperature. The solution was cooled to –20 for 15 h. The liquid phase and the solid phase was separated by vacuum filtration. The solvent was removed [at] reduced pressure. The final product was diluted 1000 times in methanol and 20 µL were injected and detected at 306 nm. The concentration of resveratrol was 6.2±0.1 mg/1 mL.

Example 3

Animals

To perform the experiments, male Wistar rats (180 to 200 g) or male Swiss mice (25 to 30 g) were used, coming from the animal house of the Federal University of Pelotas (UFPEL; Pelotas, RS). We used 5 to 8 animals per group. The animals were kept in Room 108, located in Block E, of the Vivarium of Building 12, of the PUCRS, on ventilated shelves outfitted with incoming and outgoing air filters (brand Alesco), with controlled temperature (22±1° C.) and light/dark cycle of 12 h (lights turned on at 7:00 a.m.; lights turned off at 7:00 p.m.). Within the shelves, the animals were kept in cages suitable for rodents, filled with pine shavings (changed three times a week). The animals received pelletized ration (brand Nuvilab) and filtered water (filter brand Jojaco) ad libitum. The experiments were conducted in the Applied Pharmacology Laboratory I, located in Block C, Building 12, of the PUCRS. During the experimental procedures, the laboratory temperature was maintained at 22±1° C. A minimum time of adaptation to the new environment of at least 1 hour was used, during which the animals continued to have free access to water and ration. All the experiments were carried out between 8 and 18 hours.

The experimental procedures followed the recommendations for the care of laboratory animals and the ethical standards for experimentation with conscious animals of the Guide to the Use and Care of Laboratory Animals of the National Institutes of Health (NIH) of the United States of America (NHI Publication No. 85-23, revised 1996). The principles set forth in Law No. 11,794 of 9 Oct. 2008 were respected.

Example 4

Model of Acute Inflammation by Carrageenan in the Paw of Rats

The edema of the paw was induced in accordance with the methodology described by Tratsk et al. (1997 Drymis winteri. Inflamm Res 46: 509-514). The animals were slightly anesthetized with isoflurane and received, in the right paw, 100 µl of carrageenan (300 µg/paw). The left paw received the same volume of saline and was used as the negative control. The increase in volume was evaluated by plethysmometer (Ugo Basile), at various intervals of time after the application of carrageenan (30, 60, 120, 180 and 240 min). The difference between the volume of the right paw and the left was quantified (ml) and taken as an indication of edema. In the pre-treatment (preventive) protocol, the animals were treated with saline, resveratrol (100 mg/kg) or resveratrol transported in rice oil (10 mg/kg), by oral route, 30 min prior to application of carrageenan. The same doses of resveratrol or resveratrol in rice oil, by oral route, 120 min from the application of the carrageenan, were also used in the post-treatment (therapeutic) protocol.

Figure 4:
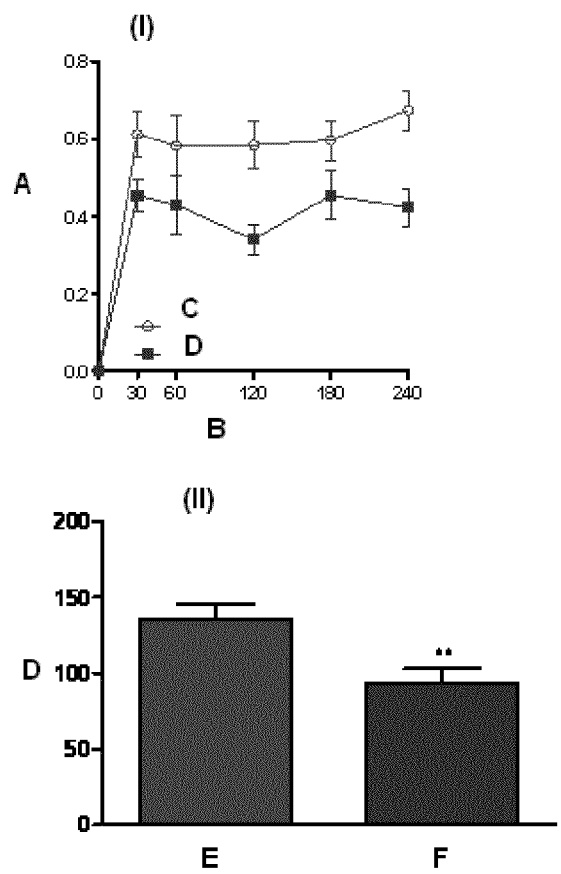
FIG. 4 shows the anti-inflammatory activity of resveratrol with preventive treatment in the acute inflammation model induced by carrageenan in rats, divided into two figures: figure (I) shows the long-term effect and figure (II) the area under the curve, where A indicates the increase in volume of the paw (ml), B indicates the time after insertion (min), C indicates the control, D indicates RSV 100 mg/kg v.o. 30 min, E indicates the area under the curve.
Figure 5:
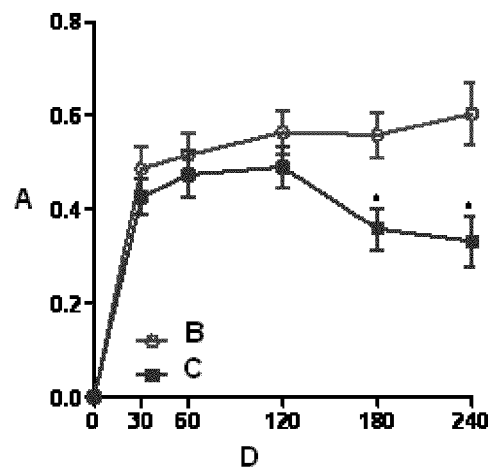
FIG. 5 shows the anti-inflammatory activity of resveratrol with therapeutic treatment in the acute inflammation model induced by carrageenan in rats, where A indicates the increase in volume of the paw (ml), B indicates the control, C indicates RSV 100 mg/kg v.o. 120 min, D indicates the time after insertion (min).
Figure 6:
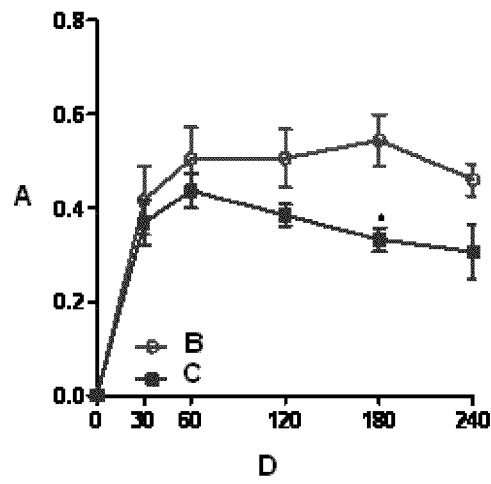
FIG. 6 shows the anti-inflammatory activity of resveratrol transported in rice oil with therapeutic treatment in the acute inflammation model induced by carrageenan in rats, where A indicates the increase in volume of the paw (ml), B indicates the control, C indicates RSV 10 mg/Kg v.o. 120 min, D indicates the time after insertion (min).

The results of FIG. 4 show that the preventive administering of resveratrol (100 mg/kg) inhibited the edema of the paw caused by carrageenan as compared to the control group, treated with saline (31±7%). Furthermore, the edema caused by the carrageenan was significantly reduced by the therapeutic administration of resveratrol (100 mg/kg), 120 min after the application of carrageenan, with inhibition of 35±8% and 45±9%, at 180 and 240 min, respectively (FIG. 5). Interestingly, the therapeutic protocol using resveratrol transported in rice oil (10 mg/kg) produced an inhibition similar to that observed with resveratrol in a dose 10 times higher (38±4%, at 180 min; FIG. 6).

Example 5

Model of Polyarthritis in Rats

The polyarthritis model was induced by CFA (1 mg/ml; 100 µl; inactivated by heat, *Mycobacterium tuberculosis*, each ml of vehicle containing 0.85 ml of paraffin oil, diluted; 1:1; oil/saline) in a total of 200 µl per paw, as described by Lorton et al. (2000), with slight modifications. In this protocol, the animals were evaluated daily in a plethysmometer (Ugo Basile), between 14 and 21 days after the application of CFA. The animals were treated with saline, resveratrol (100 mg/kg) or resveratrol transported in rice oil (10 mg/kg), by oral route, twice a day for 8 days, commencing the administration on the 14$^{th}$ day after the application of the CFA and continuing up to 21 days.

Figure 7:
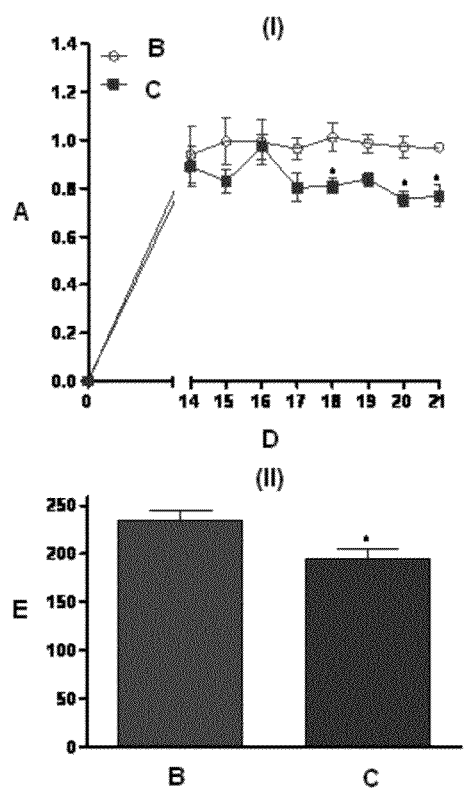
FIG. 7 shows the anti-inflammatory activity of resveratrol in the chronic inflammation model induced by CFA in rats, divided into two figures: (I) long-term effect; (II) area under the curve, where A indicates the increase in volume of the paw (ml), B indicates the control, C indicates RSV 100 mg/kg v.o., D indicates the time after insertion (min), E indicates the area under the curve.
Figure 8:
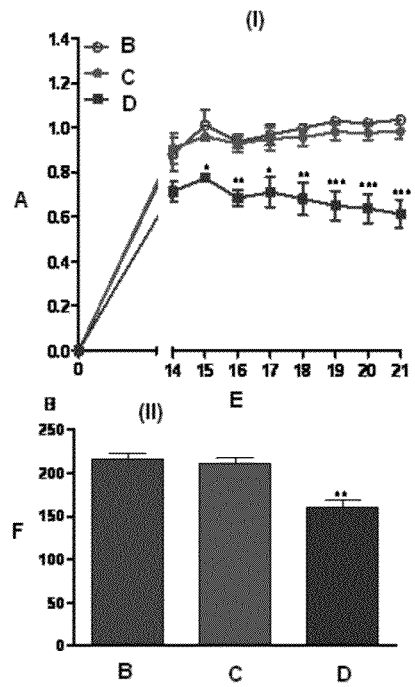
FIG. 8 shows the anti-inflammatory activity of resveratrol transported in rice oil in the chronic inflammation model induced by CFA in rats, divided into two figures: (A) long-term effect; (B) area under the curve, where A indicates the increase in volume of the paw (ml), B indicates the control, C indicates rice oil, D indicates RSVO 10 mg/kg v.o., E indicates the time after insertion (min), F indicates the area under the curve.

In this model, the chronic treatment with resveratrol (100 mg/kg) produced a distinct inhibition of the formation of edema caused by CFA (17±5%; FIG. 7). Importantly, the treatment with resveratrol transported in rice oil (10 mg/kg) produced an anti-inflammatory response greater than that obtained with resveratrol in solution (26±4%; FIG. 8). It should be noted that isolated treatment with rice oil, without resveratrol, did not cause any change in the inflammatory response elicited by CFA, which may indicate a synergistic effect resulting from the combination of resveratrol and rice oil.

Example 6

Depressive Behavior Associated with Chronic Inflammation in Mice

In this series of experiments, the depressive behavior associated with chronic inflammation in mice was evaluated. The edema of the paw was induced by the application of 50 µl/paw of CFA. The increase in volume was measured by plethysmometer, two weeks after the application of the CFA. The difference between the volume of the right and left paws was quantified (in ml) and taken as an indicator of edema.

This test considers immobility as an indicator of the depressive state (of behavioral helplessness), since the treatment of mice with antidepressive drugs causes a reduction in the time of immobility (Stéru et al., 1985 Psychopharmacology. 85:367-70). To carry out the experiments, the animals were suspended by the tail with the help of adhesive tape. The time of immobility was measured for a period of 6 min. Different groups of animals were treated with resveratrol (100 mg/kg), resveratrol transported in rice oil (10 mg/kg) or saline solution, by oral route, 1× a day for 7 days, starting the treatment 1 week after the injection of CFA.

Figure 9:
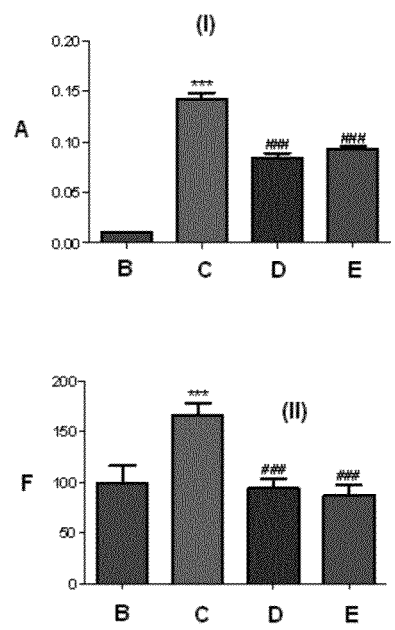
FIG. 9 shows the anti-inflammatory and antidepressant activity of resveratrol and of resveratrol transported in rice oil in the chronic inflammation model induced by CFA in rats, divided into two figures: (A) anti-inflammatory activity; (B) antidepressant activity; where A indicates the volume of edema of the paw (ml), B indicates sal+sal, C indicates CFA+sal, D indicates RSV 100 mg, E indicates RSVO 10 mg, F indicates time of immobility (s).

The edematogenic response caused by CFA in mice was significantly reduced by the treatment with both resveratrol (100 mg/kg) and resveratrol transported in rice oil (10 mg/kg). The percentages of reduction observed were: 42±4% and 35±2%, respectively. Interestingly, the depressive behavior associated with the chronic inflammation caused by CFA was expressively reduced by the treatment with both formulations, returning to the control levels the time of immobility in this model (FIG. 9).

The invention claimed is:

1. A composition comprising:
   a) vegetable oil selected from the group consisting of wheat, rice, rice bran, corn, millet, sorghum, rye, oats, barley, and combinations thereof;
   b) resveratrol and/or its derivatives;
   c) a cyclodextrin;
   d) an adsorbent; and
   e) an adequate vehicle.

2. The composition as claimed in claim 1, wherein the vegetable oil is rice bran oil.

3. The composition as claimed in claim 1, wherein the resveratrol and/or its derivatives are selected from the group consisting of trans-3,5-dimethoxy-4'-hydroxy-stilbene, trans-3,5,4"-trimethoxy-stilbene, trans-3,5-hydroxy-4'-methoxy-stilbene, trans-3,5-diacetyl-4'-hydroxy-stilbene, trans-3,5,4"-triacetyl-stilbene and trans-3,5-hydroxy-4'-acetyl-stilbene, and combinations thereof.

4. The composition as claimed in claim 1, wherein the proportion of resveratrol and/or its derivatives to vegetable oil is in the range of 1:80 to 1:90 g of resveratrol and/or its derivatives to ml of vegetable oil.

5. The composition as claimed in claim 4, wherein the proportion of resveratrol and/or its derivatives to vegetable oil is 1:83.33 g of resveratrol and/or its derivatives to ml of vegetable oil.

6. The composition as claimed in claim 1, wherein the proportion of the mixture of oil/resveratrol to cyclodextrin is in the range of 1:0.2 to 1:0.25 ml of oil/resveratrol mixture to g of cyclodextrin.

7. The composition as claimed in claim 1, wherein the cyclodextrin is chosen from the group consisting of α-cyclodextrin (α-CD), β-cyclodextrin (β-CD), γ-cyclodextrin (γ-CD), hydroxyethyl-β-CD, hydroxypropyl-β-CD, sulfobutylether-β-CD, methyl-β-CD, dimethyl-β-CD, random dimethylated-β-CD, random methylated-β-CD, carboxymethyl-β-CD, carboxymethyl ethyl-β-CD, diethyl-β-CD, tri-O-methyl-β-CD, tri-O-ethyl-β-CD, tri-O-butyryl-β-CD, tri-O-valeryl-β-CD, di-O-hexanoyl-β-CD, glucosyl-β-CD, maltosyl-β-CD, and 2-hydroxy-3-trimethyl-ammoniopropyl-β-CD, and combinations thereof.

8. A composition comprising:
   a) rice bran oil;
   b) resveratrol and/or its derivatives;
   c) a cyclodextrin;
   d) an adsorbent; and
   e) an adequate vehicle.

9. The composition as claimed in claim 8, wherein the resveratrol and/or its derivatives are selected from the group consisting of trans-3,5-dimethoxy-4'-hydroxy-stilbene, trans-3,5,4"-trimethoxy-stilbene, trans-3,5-hydroxy-4'-methoxy-stilbene, trans-3,5-diacetyl-4'-hydroxy-stilbene, trans-3,5,4"-triacetyl-stilbene and trans-3,5-hydroxy-4'-acetyl-stilbene, and combinations thereof.

10. The composition as claimed in claim 8, wherein the proportion of resveratrol and/or its derivatives to rice bran oil is in the range of 1:80 to 1:90 g of resveratrol and/or its derivatives to ml of rice bran oil.

11. The composition as claimed in claim 8, wherein the proportion of resveratrol and/or its derivatives to rice bran oil is 1:83.33 g of resveratrol and/or its derivatives to ml of rice bran oil.

12. The composition as claimed in claim 8, wherein the proportion of the mixture of rice bran oil/resveratrol to cyclodextrin is in the range of 1:0.2 to 1:0.25 ml of rice bran oil/resveratrol mixture to g of cyclodextrin.

13. The composition as claimed in claim 8, wherein the cyclodextrin is chosen from the group consisting of α-cyclodextrin (α-CD), β-cyclodextrin (β-CD), γ-cyclodextrin (γ-CD), hydroxyethyl-β-CD, hydroxypropyl-β-CD, sulfobutylether-β-CD, methyl-β-CD, dimethyl-β-CD, random dimethylated-β-CD, random methylated-β-CD, carboxymethyl-β-CD, carboxymethyl ethyl-β-CD, diethyl-β-CD, tri-O-methyl-β-CD, tri-O-ethyl-β-CD, tri-O-butyryl-β-CD, tri-O-valeryl-β-CD, di-O-hexanoyl-β-CD, glucosyl-β-CD, maltosyl-β-CD, and 2-hydroxy-3-trimethyl-ammoniopropyl-β-CD, and combinations thereof.

14. A composition comprising:
   a) rice bran oil;
   b) resveratrol and/or its derivatives, wherein the proportion of resveratrol and/or its derivatives to rice bran oil is in the range of 1:80 to 1:90 g of resveratrol and/or its derivatives to ml of rice bran oil;
   c) a cyclodextrin;
   d) an adsorbent; and
   e) an adequate vehicle.

15. The composition as claimed in claim 14, wherein the resveratrol and/or its derivatives are selected from the group consisting of trans-3,5-dimethoxy-4'-hydroxy-stilbene, trans-3,5,4"-trimethoxy-stilbene, trans-3,5-hydroxy-4'-methoxy-stilbene, trans-3,5-diacetyl-4'-hydroxy-stilbene, trans-3,5,4"-triacetyl-stilbene and trans-3,5-hydroxy-4'-acetyl-stilbene, and combinations thereof.

16. The composition as claimed in claim 14, wherein the proportion of the mixture of rice bran oil/resveratrol to cyclodextrin is in the range of 1:0.2 to 1:0.25 ml of oil/resveratrol mixture to g of cyclodextrin.

17. The composition as claimed in claim 14, wherein the proportion of resveratrol and/or its derivatives to rice bran oil is 1:83.33 g of resveratrol and/or its derivatives to ml of rice bran oil.

18. The composition as claimed in claim 14, wherein the cyclodextrin is chosen from the group consisting of α-cyclodextrin (α-CD), β-cyclodextrin (β-CD), γ-cyclodextrin (γ-CD), hydroxyethyl-β-CD, hydroxypropyl-β-CD, sulfobutylether-β-CD, methyl-β-CD, dimethyl-β-CD, random dimethylated-β-CD, random methylated-β-CD, carboxymethyl-β-CD, carboxymethyl ethyl-β-CD, diethyl-β-CD, tri-O-methyl-β-CD, tri-O-ethyl-β-CD, tri-O-butyryl-β-CD, tri-O-valeryl-β-CD, di-O-hexanoyl-β-CD, glucosyl-β-CD, maltosyl-β-CD, and 2-hydroxy-3-trimethyl-ammoniopropyl-β-CD, and combinations thereof.

19. A composition comprising:
   a) vegetable oil chosen from the group consisting of wheat, rice, rice bran, corn, millet, sorghum, rye, oats, barley, and combinations thereof;
   b) resveratrol and/or its derivatives;
   c) a cyclodextrin, wherein the proportion of the mixture of oil/resveratrol to cyclodextrin is in the range of 1:0.2 to 1:0.25 ml of oil/resveratrol mixture to g of cyclodextrin;
   d) an adsorbent; and
   e) an adequate vehicle.

20. The composition as claimed in claim 19, wherein the resveratrol and/or its derivatives are selected from the group consisting of trans-3,5-dimethoxy-4'-hydroxy-stilbene, trans-3,5,4"-trimethoxy-stilbene, trans-3,5-hydroxy-4'-methoxy-stilbene, trans-3,5-diacetyl-4'-hydroxy-stilbene, trans-3,5,4"-triacetyl-stilbene and trans-3,5-hydroxy-4'-acetyl-stilbene, and combinations thereof.

21. The composition as claimed in claim 19, wherein the proportion of resveratrol and/or its derivatives to rice bran oil is in the range of 1:80 to 1:90 g of resveratrol and/or its derivatives to ml of rice bran oil.

22. The composition as claimed in claim 19, wherein the proportion of resveratrol and/or its derivatives to vegetable oil is 1:83.33 g of resveratrol and/or its derivatives to ml of vegetable oil.

23. The composition as claimed in claim 19, wherein the cyclodextrin is chosen from the group consisting of α-cyclodextrin (α-CD), β-cyclodextrin (β-CD), γ-cyclodextrin (γ-CD), hydroxyethyl-β-CD, hydroxypropyl-β-CD, sulfobutylether-β-CD, methyl-β-CD, dimethyl-β-CD, random dimethylated-β-CD, random methylated-β-CD, carboxymethyl-β-CD, carboxymethyl ethyl-β-CD, diethyl-β-CD, tri-O-methyl-β-CD, tri-O-ethyl-β-CD, tri-O-butyryl-β-CD, tri-O-valeryl-β-CD, di-O-hexanoyl-β-CD, glucosyl-β-CD, maltosyl-β-CD, and 2-hydroxy-3-trimethyl-ammoniopropyl-β-CD, and combinations thereof.

24. A nutraceutical product comprising 0.1% to 99% wt/wt of a composition comprising:
   a) vegetable oil selected from the group consisting of wheat, rice, rice bran, corn, millet, sorghum, rye, oats, barley, and combinations thereof;
   b) resveratrol and/or its derivatives;
   c) a cyclodextrin;
   d) an adsorbent; and
   e) an adequate vehicle.

25. The nutraceutical product as claimed in claim 24, wherein the resveratrol and/or its derivatives are selected from the group consisting of trans-3,5-dimethoxy-4'-hydroxy-stilbene, trans-3,5,4"-trimethoxy-stilbene, trans-3,5-hydroxy-4'-methoxy-stilbene, trans-3,5-diacetyl-4'-hydroxy-stilbene, trans-3,5,4'-triacetyl-stilbene and trans-3,5-hydroxy-4'-acetyl-stilbene, and combinations thereof.

26. The nutraceutical product as claimed in claim 24, wherein the proportion of resveratrol and/or its derivatives to vegetable oil is in the range of 1:80 to 1:90 g of resveratrol and/or its derivatives to ml of vegetable oil.

27. A nutraceutical product comprising 0.1% to 99% wt/wt of a composition comprising:
   a) rice bran oil;
   b) resveratrol and/or its derivatives;
   c) a cyclodextrin;
   d) an adsorbent; and
   e) an adequate vehicle.

28. The nutraceutical product as claimed in claim 27, wherein the resveratrol and/or its derivatives are selected from the group consisting of trans-3,5-dimethoxy-4'-hydroxy-stilbene, trans-3,5,4'-trimethoxy-stilbene, trans-3,5-hydroxy-4'-methoxy-stilbene, trans-3,5-diacetyl-4'-hydroxy-stilbene, trans-3,5,4"-triacetyl-stilbene and trans-3,5-hydroxy-4'-acetyl-stilbene, and combinations thereof.

29. The nutraceutical product as claimed in claim 27, wherein the proportion of resveratrol and/or its derivatives to rice bran oil is in the range of 1:80 to 1:90 g of resveratrol and/or its derivatives to ml of rice bran oil.

30. A nutraceutical product comprising 0.1% to 99% wt/wt of a composition comprising:
   a) rice bran oil;
   b) resveratrol and/or its derivatives; wherein the proportion of resveratrol and/or its derivatives to rice bran oil is in the range of 1:80 to 1:90 g of resveratrol and/or its derivatives to ml of rice bran oil;
   c) a cyclodextrin;
   d) an adsorbent; and
   e) an adequate vehicle.

31. The nutraceutical product as claimed in claim 30, wherein the resveratrol and/or its derivatives are selected from the group consisting of trans-3,5-dimethoxy-4'-hydroxy-stilbene, trans-3,5,4'-trimethoxy-stilbene, trans-3,5-hydroxy-4'-methoxy-stilbene, trans-3,5-diacetyl-4'-hydroxy-stilbene, trans-3,5,4"-triacetyl-stilbene and trans-3,5-hydroxy-4'-acetyl-stilbene, and combinations thereof.

32. The nutraceutical product as claimed in claim 30, wherein the proportion of the mixture of rice bran oil/resveratrol to cyclodextrin is in the range of 1:0.2 to 1:0.25 ml of rice bran oil/resveratrol mixture to g of cyclodextrin.

33. The nutraceutical product as claimed in claim 30, wherein the cyclodextrin is chosen from the group consisting of α-cyclodextrin (α-CD), β-cyclodextrin (β-CD), γ-cyclodextrin (γ-CD), hydroxyethyl-β-CD, hydroxypropyl-β-CD, sulfobutylether-β-CD, methyl-β-CD, dimethyl-β-CD, random dimethylated-β-CD, random methylated-β-CD, carboxymethyl-β-CD, carboxymethyl ethyl-β-CD, diethyl-β-CD, tri-O-methyl-β-CD, tri-O-ethyl-β-CD, tri-O-butyryl-β-CD, tri-O-valeryl-β-CD, di-O-hexanoyl-β-CD, glucosyl-β-CD, maltosyl-β-CD, and 2-hydroxy-3-trimethyl-ammoniopropyl-β-CD, and combinations thereof.

* * * * *